(12) United States Patent
Di Cesare et al.

(10) Patent No.: US 7,098,233 B2
(45) Date of Patent: Aug. 29, 2006

(54) 5-HALO-TRYPTAMINE DERIVATIVES USED AS LIGANDS ON THE 5-HT$_6$ AND/OR 5-HT$_7$ SEROTONIN RECEPTORS

(75) Inventors: Maria Assunta Di Cesare, Pomezia (IT); Patrizia Minetti, Pomezia (IT); Giorgio Tarzia, Pomezia (IT); Gilberto Spadoni, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/481,433

(22) PCT Filed: Jun. 17, 2002

(86) PCT No.: PCT/IT02/00398

§ 371 (c)(1),
(2), (4) Date: Apr. 19, 2004

(87) PCT Pub. No.: WO03/000252

PCT Pub. Date: Jan. 3, 2003

(65) Prior Publication Data
US 2004/0235899 A1 Nov. 25, 2004

(30) Foreign Application Priority Data
Jun. 21, 2001 (IT) ......................... RM2001A0356

(51) Int. Cl.
*A61K 31/405* (2006.01)
*C07D 209/196* (2006.01)
(52) U.S. Cl. ..................................... 514/415; 548/504
(58) Field of Classification Search ................ 548/504; 514/415
See application file for complete search history.

(56) References Cited

U.S. PATENT DOCUMENTS

| | | | | |
|---|---|---|---|---|
| 2,825,734 A | * | 3/1958 | Speeter ....................... | 544/143 |
| 4,138,489 A | * | 2/1979 | Thal et al. ................. | 514/211.1 |
| 4,428,877 A | * | 1/1984 | Szantay et al. ............. | 540/520 |
| 4,980,368 A | * | 12/1990 | Thielke et al. .............. | 514/415 |
| 5,300,645 A | * | 4/1994 | Audia et al. .................. | 546/49 |
| 5,504,101 A | * | 4/1996 | Glennon ..................... | 514/415 |
| 5,688,807 A | * | 11/1997 | Audia et al. ................. | 514/285 |
| 5,726,177 A | * | 3/1998 | Halazy et al. ......... | 514/254.09 |
| 6,403,808 B1 | * | 6/2002 | Glennon et al. ............ | 548/491 |

FOREIGN PATENT DOCUMENTS

| | | |
|---|---|---|
| EP | 0 937 715 A | 8/1999 |
| WO | 00/34242 A | 6/2000 |
| WO | 00/63203 A | 10/2000 |
| WO | 01/12629 A | 2/2001 |
| WO | WO 2004041781 A1 * | 5/2004 |

OTHER PUBLICATIONS

Glennon, R., et al., "2-Substituted Tryptamines: Agents with Selectivity for 5-HT6 Serotonin Receptors," J. Med. Chem., vol. 43(5), pp. 1011-1018 (Mar. 2000), at p. 1012, Scheme 1; p. 1013, Table 1 (compound 8, "EMDT"); & p. 1014, Table 2 (5HT7 and 5HT6).*
Spadoni, G., et al., "2-Substituted 5-Methyoxy-N-acyltryptamines: Synthesis, Binding Affinity for the Melatonin Receptor, and Evaluation of the Biological Activity," J. Med. Chem., vol. 36(25), pp. 4069-4074 (Dec. 1993) at p. 4070, col. 1, Scheme 1.*
Branchek, T., "5-HT6 Receptors as Emerging Targets for Drug Discovery," Ann. Rev. Pharm. Tox., vol. 40, pp. 319-334 (2000), at Abstract; p. 322, line 40 to p. 323, line 3; and p. 328, lines 11-30.*
Worthen, D., et al., "Endogenous indoles as novel polyamine site ligands at the N-methyl-D-aspartate receptor complex," Brian Research, vol. 890(2), pp. 343-346 (Feb. 2, 2001), at p. 344, Table 1; also p. 343, lines 6-8.*
Russell, M., and Dias, R., "Memories are Made of this (Perhaps): A Review of Serotonin 5-HT6 Receptor Ligands and Their Biological Functions," Curr. Top. Med. Chem., vol. 2(6), pp. 643-654 (Jun. 2002), at p. 645, col. 1, lines 22-29 and Figure 1.*
Glennon, R., "Higher-End Serotonin Receptors: 5-HT5, 5-HT6 and 5-HT7," J. Med. Chem., vol. 46(14), pp. 2795-2812 (Jul. 3, 2003), at p. 2795, col. 2, lines 14-22.*
Schmitz, D., et al., "Serotonin reduces synaptic excitation in the superficial medial entorhinal cortex of the rat via a presynaptic mechanism," J. Physiology, vol. 508 (Pt 1), pp. 119-129 (Apr. 1998), at p. 119, col. 2, lines 2-6; p. 120, lines 40-41.*
Gungor, T., et al., "N6-substituted Adenosine Receptor Agonists. Synthesis and Pharmacological Activity as Potent Antinociceptive Agents," J. Med. Chem., vol. 37(25), pp. 4307-4316 (1994), at p. 4310, Table 2 (cmpds 15b and 6b).*
Benington, F., et al., "Synthesis of Some 5- and 6-Chloro, 5-Methyl, and 5,6,7-Trimethyl Derivatives of Tryptamine," J. Org. Chem., vol. 25(9), pp. 1542-1547 (Sep. 1960), at p. 1543, Chart I ("compound VIII"); p. 1545, col. 2, lines 61-72.*

(Continued)

Primary Examiner—Kamal A. Saeed
(74) Attorney, Agent, or Firm—Nixon & Vanderhye P.C.

(57) ABSTRACT

Compounds of Formula (I): (I); wherein: $R_1$ and $R_2$ either the same or different, are H or linear or branched $C_1$–$C_6$ alkyl; $R_3$=linear or branched $C_1$–$C_6$ alkyl; $R_4$=halogen, and pharmaceutically acceptable salts thereof are useful as active ingredients in the preparation of medicaments used as ligands of the 5-HT$_6$ and/or 5-HT$_7$ serotoninergic receptors.

19 Claims, No Drawings

OTHER PUBLICATIONS

Lee et al; "5-HT6 Serotonin Receptor Binding Affinities of N1-Benzenesulfonyl and Related Tryptamines"; Medicinal Chemistry Reserch, Birkhaeuser, Boston, US, vol. 4, No. 10, 2000, pp. 230-242, XP001079522.

Chapman et al; "5-Substituted-2-Methyltryptamines and Their N-Mono-and N,N-Dialkyl Derivatives" J. Chem. Soc., Feb. 1965, pp. 1424-1428, XP00109902.

* cited by examiner

5-HALO-TRYPTAMINE DERIVATIVES USED AS LIGANDS ON THE 5-HT$_6$ AND/OR 5-HT$_7$ SEROTONIN RECEPTORS

This application is the U.S. national phase of international application PCT/IT02/00398, filed in English on 17 Jun. 2002, which designated the U.S. PCT/IT02/00398 claims priority to IT Application No. RM2001A000356 filed 21 Jun. 2001. The entire contents of these applications are incorporated herein by reference.

The invention described herein relates to 5-halogenated tryptamine derivatives useful as ligands of the 5-HT$_6$ and/or 5-HT$_7$ serotonin receptors, processes for their preparation, their use as medicaments, in particular for the treatment of nervous system pathologies associated with serotonin level deficit, systemic pathologies involving the cardiovascular system, the gastrointestinal tract and the pharmaceutical compositions comprising them.

BACKGROUND OF THE INVENTION

Over the past 10 years, molecular cloning has revealed 14 serotonin subtypes that have been divided into 7 subfamilies. The large multiplicity of serotonin receptors has been suggested to be a direct result of the evolutionary age of 5-HT system. With the exception of 5-HT$_3$ receptors which are ligand-gated ion channels, all of receptors are members of the serotonin receptor superfamily belonging to a large class of receptors linked to their effector functions via G-protein. (Gerhardt, C. C. et al., *Brain Res.* 746:207–219, 1997; Hoyer, D. et al., *Neuropharmacol.* 36;419–428, 1997).

In 1994, 5-HT$_6$ serotonin receptors were discovered on pig nucleus caudatum and cerebellum membranes. Since then, 5-HT$_6$ serotonin receptors have been observed in the olfactory tubercle, frontal and entorinal cortex, nucleus accumbens, striatum, hippocampus and in the molecular layer of the cerebellum. 5-HT$_6$ serotonin receptors appear to be almost exclusively present in the brain and in 5-HT projection fields and not in the 5-HT neurons of raphe nuclei suggesting that 5-HT$_6$ receptors probably have a postsynaptic role. It has been further discovered that 5-HT$_6$ receptors are members of the G-protein superfamily and they are positively coupled to an adenylate cyclase second messenger system.

Serotonin binding to the 5-HT$_6$ receptors induces an activation of the adenylate cyclase enzyme, with concomitant increase of intracellular cAMP levels. The recent discovery of 5-HT$_6$ serotonin receptors has stimulated research into 5-HT$_6$-selective ligands to demonstrate uniqueness of the new receptor subfamily and its own exact clinical significance. It is actually known that many psychoactive drugs (antidepressants, antipsychotics) exhibit high affinity for 5-HT$_6$, however, without selectivity (Monsma, F. J. et al., *Molecular Pharmacology* 43.320–327, 1993; Roth, B. L. et al., *J. Pharmacol. Exp. Ther.* 268, 1403–1410; 1994) and that 5-HT$_6$ receptors might modulate cholinergic neurotransmission in the central nervous system. Furthermore, 5-HT$_6$ receptors displayed on GABA-containing neurons in the striatum and on glutamate-containing neurons of hippocampus have been suggested to mediate endogenous serotonin actions. Thus, ligands for 5-HT$_6$ receptors might be useful to treat: motor disorders, depression, anxiety, mood disorders, memory disorders, Huntington's disease, Parkinson's disease and Alzheimer's disease. (Branchek, T. A. and Blackburn, T. P., *Annu. Rev. Pharm. Toxicol.* 40: 319–34, 2000).

5-HT$_7$ serotonin receptors were identified in several rodent and human tissues. In rat brain, 5-HT$_7$ receptors appear with particularly high distribution in hypothalamus, thalamus and hippocampus, while lower 5-HT$_7$ receptor RNAm levels were found in the cerebral cortex, striatum, olfactory bulb and olfactory tubercle. The presence of 5-HT$_7$ receptor RNAm is not limited to the brain, it has also been found in peripheral tissues (spleen, stomach, intestine, heart, coronary artery). 5-HT$_7$ receptors are functionally coupled to adenylate cyclase enzymatic system. Pharmacological in vitro evidences demonstrate increase of endocellular cAMP levels following 5-HT$_7$ receptor stimulation. As with 5-HT$_6$ serotonin receptors, the clinical value of 5-HT$_7$ receptors is not currently known (Sleight, A. J., Boess, F. G., Bourson, A., Sibley, D. R., Monsma, F. J., 1997 *DN&P* 10 (4): 214–224). It has been suggested that 5-HT$_7$ receptors might be involved in the mechanisms regulating blood pressure. 5-HT$_7$ receptors' high distribution on the blood vessels and pharmacological data demonstrating vasodilatation following serotonin binding to the 5-HT$_7$ receptors suggest utilization of 5-HT$_7$ ligands as hypotensive agents (Martin, G. R. and Wilson, R., (1995) *British J. Pharmacol.* 114: 383P). Furthermore, it was previously demonstrated that 5-HT$_7$ receptors, abundantly present in the hypothalamus, are implicated in the control of circadian rhythm of spontanieus neuronal electrical activity in the central nervous system (Lowenberg, T. N. et al., *Neuron* (1993) 11:449–58).

Thus, 5-HT$_7$ ligands may be modulator agents of many processes regulated by circadian rhythm particularly sleep cycle whose desynchronization induces sleep disorders. Other evidences demonstrate that 5-HT$_7$ receptors might be involved in the pathogenesis and treatment of depression. The observation that, 5-HT$_7$ receptor binding sites in rat hypothalamus determine a down-regulation following chronic treatment with antidepressant Fluoxetine, has supported this therapeutic indication (Sleight, A. J. et al., *Mol. Pharm.* (1996), 47: 99–103). The strict classical notions of neurotransmitter disregulation hypothesis that associate depression with a deficiency of available neurotrasmitter or subresponsivity of mainly noradrenergic and/or serotoninergic receptor systems have recently been expanded to include disturbances in biological rhythm regulation. Impairment of the efficiency of rhythm maintenance or rhythm desynchronization has been suggested by many to lead to mental fatigue and depression (Goodwin F. K., Wirz-Justice A., Wehr T. A., 1982. *It Costa Ragni (eds.), Typical and atypical antidepressant: Clinical pratical*).

Although melatonin is generally thought to be a primary modulator of circadian functions, serotonin also plays a critical role, particularly acting on 5-HT$_{1a}$, 5-HT$_{1b}$, 5-HT$_{2a}$, 5-HT$_7$ subtypes in the soprachiasmatic nucleus of the hypothalamus (Van Den Pol, A. N., Dudek, F. E., (1993) *Neurosciensce* 56:793–811; Mullins, U. L., et al., (1999): *Neuropsychopharmacology* 21, (3) 352–367).

Contemporary localization of 5-HT$_6$ and 5-HT$_7$ receptor sites, although with different density of distribution, in brain areas (hippocampus, frontal cortex) implicated functionally in the attention and learning processes and that same ability on the part of both receptors to increase endocellular cAMP levels following their stimulation have suggested that agents binding both 5-HT$_6$ and 5-HT$_7$ receptor might modulate neuronal plasticity mechanism underlying the acquisition and subsequently the learning processes of an individual.

Ligands with contemporary affinity for 5-HT$_6$ and 5-HT$_7$ receptors might have a therapeutic use in conditions requiring an improvement in cognitive processes (Menese, A., (1999) *Neurosci. Biobehav. Rev.*, 23 (8):1111–25).

Probable use of 5-HT$_7$-ligands in treatment of irritable bowel disease has been suggested by recent evidence. Gastric hypomotility is thought to be one of the mechanisms underlying pathophysiological mechanism of this syndrome and remains an attractive therapeutic target. Actually a new generation of prokinetics includes 5-HT$_4$ receptor ligands (tegaserod, prucalopride). Preliminary evidence arouses interest in research of 5-HT$_7$ receptor ligands to be directed toward the above therapeutic target (De Ponti, F., Tonini, M., (2001) *Drugs*, 61 (3):317–332). In fact, the observation that 5-HT$_7$ receptors mediate smooth muscle relaxation and 5-HT$_7$ binding sites localization on intestine tissue should suggest therapeutic use of 5-HT$_7$ receptor ligands.

At the present, compounds with affinity for the 5-HT$_6$ receptor have been identified belonging to different chemical classes. For example, EP 0 815 861 and EP 0 930 302, Hoffmann-La Roche, describe sulphonamides and benzosulphonate derivatives as selective ligands for the above-mentioned receptors; WO 98/27058, SmithKline Beecham, describe carboxyamide indole derivatives as 5-HT$_6$ receptor antagonists, whilst WO 98/27081 and WO 99/42465, Smith-Kline Beecham, describe, amongst others, sulphonamide derivatives, as does U.S. Pat. No. 6,187,805, Merck Sharp and Dohme; WO 00/12623, SmithKline Beecham, describes sulphonate and sulphonamidederivatives: WO 00/37452, Merck Patent, describes sulphonyloxazolylamines: WO 00/63203 and U.S. Pat. No. 6,133,287, Allelix Biopharmaceutical Inc., describe piperidinoindoles as acting as 5-HT$_6$ antagonists.

Tryptamine derivatives are well-known for several pharmacological uses. WO 97/06140 describes their use for the treatment of pathologies correlated with melatonin disturbances; WO 97/46525 and WO 98/23587 as selective ligands of the 5-HT$_{1D}$ receptor and their use in the treatment of migraine; WO 97/48680 for the treatment of vasospasms; WO 98/06695 for dermatological treatments; WO 98/47868 as combined activity antagonists of various subtypes of the 5-HT$_1$ receptor; WO 00/11619 as selective antagonists of the 5-HT$_{2A}$ receptor; WO 99/51576 for the treatment of nervous disorders associated with the serotoninergic system; WO 99/54301 as antibacteric agents; WO 00/37441 for the treatment of cardiovascular, ischaemic, parasitic, inflammatory, neurodegenerative diseases, myopathy and sickle-cell anemia; WO 00/78716 and WO 00/44721 as active agents on the adrenergic system.

Other tryptamine derivatives are noted for their activity against serotoninergic receptors different from 5-HT$_6$, for example WO 95/14004, WO 95/24200, WO 96/26922, WO 96/26923, WO 97/13512, WO 99/51576, EP 1023898 and WO 00/52002.

Regarding compounds with specific activity against the 5-HT$_6$ receptor, WO 99/47516, Slassi et. al. describes 1-acyl or 1-sulphonylindole substituted at position 3 with an alkylpyrrolidine with affinity for the 5-HT$_6$ receptor. WO 99/65906, Allelix Biopharmaceuticals Inc. discloses bicyclic piperidines and piperazines linked to an indole residue as inhibitors of the 5-HT$_6$ receptor.

Patent application WO 00/34242, Virginia Commonwealth University, discloses serotonin derivatives with increased affinity and selectivity for the 5-HT$_6$ receptor. Patent application WO 00/63203, Allelix Biopharmaceuticals Inc., discloses 1-acyl or 1-sulphonylindoles, substituted at position 3 with a piperidine, having affinity for the 5-HT$_6$ receptor.

As for the 5-HT$_7$ receptor, WO 00/37082, Smithkline Beecham, discloses the use of 5-HT$_7$ receptor antagonists described in WO 97/29097, WO 98/48681 and WO 97/49695 for the treatment of neuronal degenerations resulting from ischemic events; EP 0 998 923, BASF, discloses the use of 5-HT$_7$ receptor antagonists in the prevention of ischemias, in particular infarction; WO 99/54303 and WO 98/00400, Meiji, discloses tetrahydrobenzindoles for the treatment of mental and circulatory disorders.

Abstract of the Invention

The present invention relates to tryptamine based ligands with affinity for the 5-HT$_6$ and/or 5-HT$_7$ serotonin receptors. From a therapeutic point of view, these agents can be used for the treatment of nervous system pathologies, associated with serotonin level deficit, systemic pathologies involving the cardiocirculatory system (hypertension) and gastrointestinal tract (irritable bowel disease).

It is known that many disorders of the central nervous system are effectively treated by the use of drugs which can interact specifically with serotonin receptors, and for this reason, clinically approved for the treatment of migraine, depression, hypertension, psychosis and mental fatigue, sleep disorders and other effects derived from the desynchronisation of circadian rhythms.

It has now been found that compounds of Formula (I)

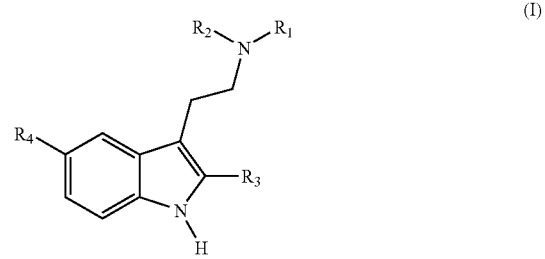

wherein:
R$_1$ and R$_2$, the same or different, are H or C$_1$–C$_6$ linear or branched alkyl;
R$_3$=C$_1$–C$_6$ linear or branched alkyl;
R$_4$=halogen;
have affinity for the 5-HT$_6$ and/or 5-HT$_7$ receptors.

Accordingly, it is an object of the present invention the use of compounds of Formula (I) above and the pharmaceutically acceptable salts thereof for the preparation of medicaments useful as ligands of the 5-HT$_6$ and/or 5-HT$_7$ serotoninergic receptor, in particular for the treatment of nervous system pathologies associated with serotonin level deficit, systemic pathologies involving the cardiocirculatory system, in particular hypertension; the gastrointestinal tract, in particular irritable bowel disease. Other objects of the present invention are new compounds of Formula (I) from which are excluded compounds where R$_4$ is fluoro, chloro or bromo, R$_3$ is methyl or ethyl, R$_1$ and R$_2$, the same or different, are hydrogen and methyl; a process for the preparation of said new compounds of Formula (I), their use as medicaments, in particular for the treatment of nervous system pathologies associated with serotonin level deficit, systemic pathologies involving the cardiovascular system, in particular hypertension; the gastrointestinal tract, in particular irritable bowel disease and pharmaceutical compositions containing said compounds as active ingredients.

DETAILED DESCRIPTION OF THE INVENTION

In the compounds of Formula (I), the terms $C_1$–$C_6$ alkyl are intended to mean the methyl, ethyl, propyl, isopropyl, butyl, sec-butyl, tert-butyl, pentyl, hexyl, and all the possible isomers, preferably methyl and ethyl.

For halogens, the meaning is fluoro, chloro, bromo and iodio, preferably chloro and bromo.

Among the Formula (I) compounds, a first preferred group comprises those compounds in which the groups $R_1$ and $R_2$ are the same, particularly methyl.

A second preferred group comprises Formula (I) compounds wherein $R_3$ is alkyl, as defined above, in particular methyl or ethyl, and $R_4$ is chloro. Formula (I) compounds wherein $R_4$ is chloro have selective affinity for 5-$HT_6$ serotonin receptor, therefore are useful for the preparation of medicaments useful as ligands of the 5-$HT_6$, for example for the treatment of depression, mood disorders, psychosis, schizophrenia, motor disorders, cognitive disorders, Parkinson's disease, Alzheimer's disease, Hungtinton's disease.

A third preferred group comprises Formula (I) compounds wherein $R_3$ is alkyl, as defined above, in particular methyl, and $R_4$ is bromo.

Particularly, when $R_4$ is bromo the molecule also acquires affinity for the 5-$HT_7$ receptor subtype.

By virtue of this property, the compounds are indicated in the treatment of depression, migraine, hypertension, in particular for the improvement of the individual learning process, to counteract the desynchronisation of the biological rhythms and the many alterations derived therefrom (mental fatigue, depression, sleep disorders).

Particularly preferred are the compounds 5-bromo-2-methyl-N,N-dimethyltryptamine (ST 1938), 5-chloro-2-ethyl-N,N-dimethyltryptamine (ST 2253) and 5-chloro-2-methyl-N,N-dimethyltry-ptamine (ST 1936).

Formula (I) compounds wherein $R_3$ is methyl, $R_1$ and $R_2$ are the same or different and are hydrogen and methyl are described in Chapman, N. B. et. al., *J. Chem. Soc.* 1965; 1424–1428.

The compounds according to the present invention, can be prepared by the process illustrated in the following scheme according to procedures reported in the literature for analogous compounds (Spadoni, G. et. al., *J. Med. Chem.*, 1993; 36 (25): 4069–74).

Those of ordinary skill in the art will be able to choose the correct starting compounds and the corresponding reagents and reaction conditions in relation to the desired final product relating to the above mentioned Formula (I).

The process according to the present invention is carried out according to the scheme 1 reported below.

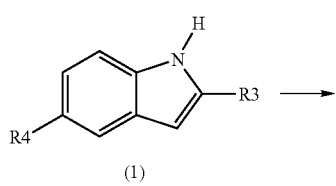

(1)

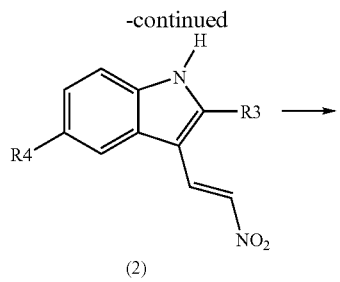

(2)

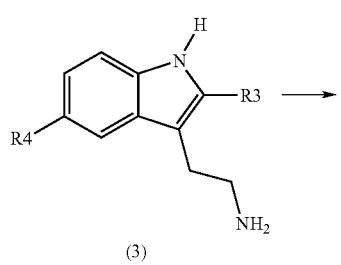

(3)

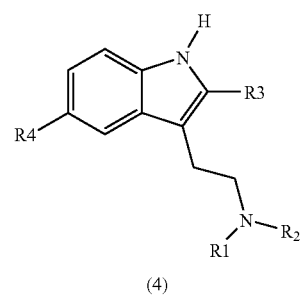

(4)

The starting compound, 5-halo-2-alkyl-indole is commercially available or can be prepared by analogy as described in *J. Med. Chem.* 1993, 36, 4069, but see also *JOC* 1994, 59, 6372–6377.

The Formula (1) compound is reacted with 1-dimethylamino-2-nitoethylene, which is commercially available. The molar ratios are not critical, as an example it is convenient to react the compounds in equimolar amounts, even if an excess of one or the other could be envisaged in relation to the different Formula (I) final products. The reaction is carried out in trifluoroacetic acid, at a temperature and for a time that can be chosen in relation to the reagents, their concentrations and the solvents used. Suitably, the reaction can proceed at low temperatures, for example 0° C., up to a temperature compatible with the reaction conditions and the absence or reduced quantities of secondary products or of degradation, and for times from a few minutes to several hours.

Compound (2), if desired, is isolated from the reaction medium using conventional techniques known by those skilled in the art, it is then subjected to reduction of the ethyl double bond adjacent to the nitro group, to give the corresponding saturated derivative (3). For the considerations relating to the reaction conditions, those skilled in the art could gain these from the preceding paragraph.

The final step gives the functionalisation of the primary amino group with the groups given in the definitions for $R_1$ and $R_3$. This is done by conventional methods noted in the literature, for example *J. Org. Chem.* 37, 1673–1674 (1972).

The following examples further illustrate the invention.

EXAMPLE 1

(E)-5-Bromo-2-methyl-3-(2-nitroethenyl)-1H-indole

To a solution of 0.58 g of 1-(dimethylamine)-2-nitroethylene (5 mmol) in 5 mL of trifluoroacetic acid, stirred and cooled to 0° C., 1.05 g (5 mmol) of 5-bromo-2-methyl-indole is added and the resulting mixture is left to react at room temperature, under nitrogen, for 30 minutes. The reaction mixture is then placed into an ice-water bath. The aqueous solution is extracted with ethyl acetate and the organic phases combined, then washed with a saturated bicarbonate solution, and then water and finally dried over anhydrous sodium sulphate. After filtration, the solvent is removed at low pressure, leaving a solid, orange-coloured residue, which is then suspended in an ethyl acetate—ether mixture and filtered.

Yield: 89% Rf=0.3 (cyclohexane/EtOAc :1) M.p.: 196–198° C. (dec.) $^1$H- NMR (200 MHz)(DMSO-d6): δ 2.59 (s, 3H), 7.34 (m, 2H), 7.97 (d, 1H, J=13.2 Hz), 8.06 (m, 1H), 8.26 (d, 1H, J=13.2 Hz) EIMS: m/z 280, 282 (M+), 154 (100)

5-bromo-2-methyltryptamine hydrochloride

A solution of nitroethenylindole (2) (1.7 g, 6 mmol), in 25 mL of anhydrous THF, is added dropwise to a suspension, under nitrogen at 0° C., of LiAlH$_4$ (1.2 g, 36 mmol) in THF (6.5 mL) and the resulting mixture is stirred for 5 hours at room temperature. After cooling to 0° C., the excess LiAlH$_4$ is destroyed by the careful addition of water and the resulting suspension filtered through celite. The solvent is evaporated under vacuum, the residue acidified with 2N HCl and then partitioned with water and ethyl acetate. The aqueous phase is then alkalinized with 6N NaOH and extracted 3 times with ethyl acetate. The combined organic phases are washed with brine, dried over anhydrous sodium sulphate and concentrated under vacuum. The resulting free amine is then transformed into the hydrochloride salt by the addition of a solution of HCl in anhydrous methanol. The salt is then purified by crystallization in ethyl acetate.

Yield: 69%. $^1$H NMR (200 MHz, (DMSO-d6): δ 2.33 (s, 3H), 7.09 (dd, 1H, J=1.9 and J=8.3 Hz), 7.21 (d, 1H, J=8.3 Hz), 7.65 (d, 1H, J=1.5 Hz), 7.94 (br, s, 3H), 11.15 (s, 1H), 7.94 (br, s, 3H), 11.15 (s, 1H).

5-bromo-2-methyl-N,N-dimethyltryptamine (ST 1938)

A 40% solution of HCHO (0.95 mL) in 16 mL of MeOH, is added dropwise to a stirred solution of 5-bromo-2-methyltryptamine (0.8 g, 3.16 mmol). AcOH (0.47 mL) and NaCNBH$_4$ (0.35 g). This is let to react for 2.5 hours at room temperature under stirring; 5 mL of an aqueous saturated solution of K$_2$CO$_3$ is then added; methanol is evaporated under vacuum and the aqueous phase extracted with ethyl acetate.

The organic phases are dried over anhydrous sodium sulphate, and after evaporation of the solvent under vacuum an orange coloured oil is obtained, which is purified by filtration through silica gel and subsequent crystallisation from dichloromethane-hexane.

Yield: 56% M.p.: 135–136° C. Rf=0.52 (CH$_2$Cl$_2$/MeOH/TEA 9:0,4:0.4) $^1$H NMR (200 MHz, (CDCl$_3$): δ 2.35 (s, 6H), 2.37 (s, 3H), 2.44–2.52 (m, 2H), 2.78–2.86 (m, 2H), 7.11 (d, 1H, J=8.5 Hz), 7.18 (dd, 1H, J=1.6 e J=8.5 Hz), 7.60 (d, 1H, J=1.6 Hz), 7.95 (br s, 1H). EIMS: m/z 280, 282 (M$^+$), 222, 224 (100).

EXAMPLE 2

Following the method described and in accordance with the scheme and example above, the following compounds were prepared:

(E)-5-chloro-2-methyl-3-(2-nitroethenyl)-1H-indole

Orange solid Yield: 85%; M.p. 191–193° C. $^1$H NMR (200 MHz, (acetone-d$_6$): δ 2.68 (s, 3H), 7.21 (dd, 1H, J=1.95 and J=8.5 Hz), 7.5 (d, 1H, J=8.5 Hz), 7.85 (d, 1H, J=13.3 Hz), 7.86 (d, 1H, J=1.95 Hz), 8.30 (d, 1H, J=13.3 Hz); EIMS: m/z 236 (M$^+$), 154 (100).

5-chloro-2-methyltryptamine hydrochloride

Beige solid crystalline precipitated from EtOH/Et$_2$O.

Yield: 72% $^1$H NMR (200 MHz, (DMSO-d$_6$): δ 2.33 (s, 3H), 6.97 (dd, 1H, J=1.9 and J=8.3 Hz), 7.25 (d, 1H, J=8.3 Hz), 7.52 (d, 1H, J=1.5 Hz), 8.03 (br, s, 3H), 11.15 (s, 1H).

5-chloro-2-methyl-N,N-dimethyltryptamine (ST 1936)

White solid; Yield: 75%; M.p.=126–127° C. $^1$H NMR (200 MHz, CDCl$_3$): δ 2.35 (s, 6H), 2.38 (s, 3H), 2.44–2.52 (m, 2H), 2.79–2.87 (m, 2H), 7.05 (d, 1H, J=1.9 and J=8.6 Hz), 7.17 (d, 1H, J=8.2 Hz), 7.45 (d, 1H, J=1.9 Hz), 7.86 (br s, 1H) EIMS: m/z 236 (M$^+$), 178 (100).

EXAMPLE 3

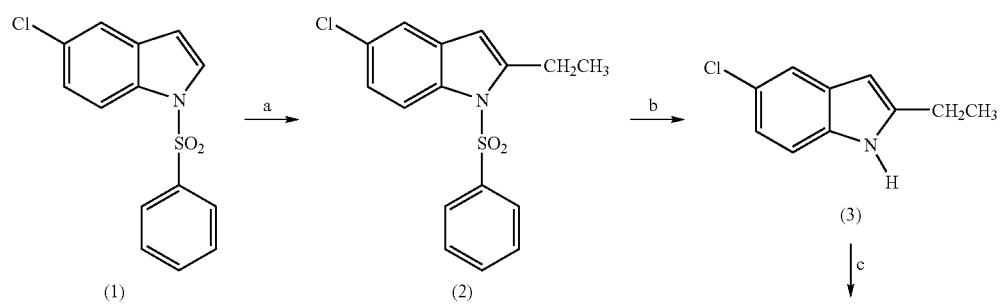

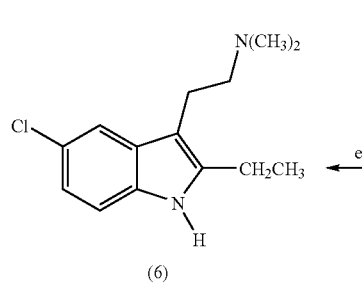 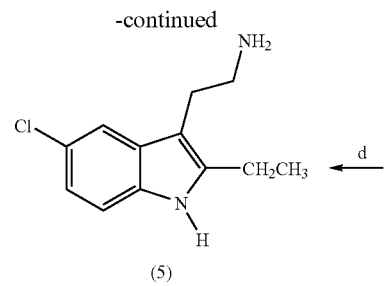 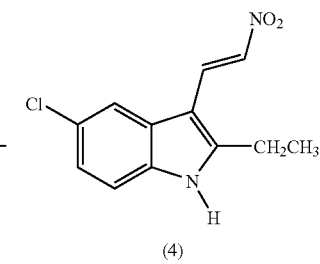

Reagents: (a) t-BuLi,THF,−20° C.; EtI, −78° to room temperature, 2 h; (b) 2N NaOH, MeOH, reflux, 40 h; (c) 1-(dimethylamino)-2nitroethylene, TFA, 0° C., 0.5 h; (d) LiAlH$_4$, THF, room temperature, 6 h; (e) NaCNBH$_3$, 40%, HCHO, MeOH, AcOH, room temperature, 2.5 h.

N-(Benzensulfonyl)-5-chloro-2-ethylindole (2)

t-BuLi (3.7 mL of 1.7 M solution in pentane) was added dropwise to a solution of N-(benzensulfonyl)-5-chloroindole (1) (J. Org. Chem. 1981, 46, 3859) (1.5 g, 5.14 mmol) in THF (35 mL) at −70° C., under a nitrogen atmosphere. The mixture was stirred for 15 min, allowed to warm to room temperature over 20 min, cooled to −70° C., and treated with a solution of ethyl iodide (0.84 mL, 10.5 mmol) in dry THF (5 mL). The mixture was stirred at −78° C. for 1 h, allowed to warm to room temperature, stirred for 2 h, poured into ice (15 g), and a saturated aqueous NH$_4$Cl solution and then extracted with ether (3×20 mL). The combined organic extracts were washed with brine, dried (Na$_2$SO$_4$) and evaporated in vacuo to give a residue which was purified by flash chromatography (silica gel, cyclohexane/ethyl acetate, 8:2) and crystallization from ethylacetate/cyclohexane.

Yield: 80% M.p.: 108° C. (dec.) $^1$H-NMR ( MHz,) (CDCl$_3$): δ 1.33 (τ, 3H), 3.01 (q, 2H), 6.35 (s, 1H), 7.23 (dd, 1H), 7.39–7.74 (m, 6H), 8.11 (d, 1H) EIMS: m/z 319 (M$^+$); 178, 143 (100%)

5-Chloro-2-ethylindole (3)

A mixture of 2 (1.3 g, 4.07 mmol), 2N NaOH (12 mL), and MeOH (62 mL) was refluxed for 40 h. The organic solvent was evaporated and the remaining residue was extracted with EtOAc. The combined extract were washed with brine, dried (Na$_2$SO$_4$) and evaporated in vacuo to give a residue which was purified by flash chromatography (silica gel, cyclohexane/ethyl acetate, 8:2) and crystallization from ether/cyclohexane.

M.p.=89° C. Yield 90% $^1$H NMR (CDCl$_3$) δ 1.35 (t, 3H), 2.79 (q, 2H), 6.19 (s, 1H), 7.06 (dd, 1H), 7.21 (d, 1H), 7.49 (s, 1H), 7.92 (br s, 1H) EIMS: m/z 179 (M$^+$); 164 (100)

(E)-5-Chloro-2-ethyl-3-(2-nitroethenyl)-1H-indole (4)

The indole 3 (5 mmol) was added to a stirred ice-cooled solution of 1-(dimethylamino)-2-nitroethylene (0.58 g, 5 mmol) in trifluoroacetic acid (5 mL). The mixture was stirred at room temperature under N$_2$, for 0.5 h and then poured onto ice water. The aqueous solution was extracted with ethyl acetate, the combined organic layers were washed with a saturated NaHCO$_3$ solution and then with water. After drying over Na$_2$SO$_4$, the solvent was evaporated under reduced pressure to give a crude orange solid which was suspended in a mixture of EtOAc-Et$_2$O and filtered, or chromatographed on silica gel (cyclohexane/EtOAc, 1:1, as eluent).

Yield:89% M.p.: 188° C. dec. $^1$H(CDCl$_3$) δ 1.42 (t,3H), 3.02 (q,2H), 7.21–7.34 (m,2H), 7.68 (m,1H), 7.72 (d, 1H), 8.3 (d,1H), 8.68 (br s,1H) EIMS:m/z 250(M+), 203, 188 (100)

5-Chloro-2-ethyltryptamine (5)

A solution of the nitroethenylindole 4 (6 mmol) in dry THF (25 mL) was added portionwise to a stirred ice-cooled suspension of LiAlH$_4$ (1.2 g, 36 mmol) in dry THF (65 mL) under nitrogen and the mixture was stirred at room temperature for 5 h. After cooling to 0° C., the unreacted LiMAlH$_4$ was destroyed by careful addition of water. The resulting mixture was filtered through a Celite® pad; the filtrate was concentrated in vacuo, then acidified with 2N HCl and partitioned between water and ethyl acetate. The aqueous phase was made alkaline with 6N NaOH and then extracted (3×) with EtOAc; the combined organic layers were washed with brine, dried (Na$_2$SO$_4$), and concentrated under reduced pressure to give a crude oily amine.

(oil); EIMS: m/z 222 (M$^+$); 192 (100), 177

5-Chloro-2-ethyl-N,N-dimethyltryptamine (6) (ST 2253)

40% HCHO (0.95 mL) in MeOH (16 mL) was added dropwise to a stirred cooled (0° C.) solution of (5) (3.16 mmol), AcOH (0.47 mL) and sodium cyanoborohydride (0.35 g). The resulting mixture was allowed to stir at 25° C. for 2.5 h. A saturated aqueous solution of K$_2$CO$_3$ (5 mL) was added, MeOH was removed in vacuo and the aqueous phase was extracted with EtOAc. After drying over Na$_2$SO$_4$, the solvent was evaporated under reduced pressure to give a crude residue which was purified by filtration on silica gel.

(Amorphous solid); $^1$H NMR (CDCl$_3$) δ 1.3 (t, 3H); 2.42 (s, 6H); 2.55 (m, 2H), 2.83 (m, 4H), 7.06 (dd, 1H), 7.19 (d, 1H),7.45 (m, 1H), 7.88 (br s, 1H) EIMS: m/z 250 (M$^+$); 192, 177, 58 (100)

The compounds according to the present invention are ligands of the 5-HT$_6$ and/or 5-HT$_7$ serotoninergic receptors; therefore they are useful as medicaments, in particular for the treatment of nervous system pathologies associated with serotonin level deficit, systemic pathologies involving the cardiocirculatory system (hypertension), the gastrointestinal tract (irritable bowel disease).

Amongst the pathologies treated with the compounds of the present invention are: migraine, depression, hypertension, psychosis and other processes involved with functional alterations, brought about by the desynchronisation and/or loss of circadian rhythms (wake/sleep cycle, melatonin synthesis).

Regarding one of the preferred groups of the Formula (I) compounds, in which $R_3$ is methyl and $R_4$ is bromo or chloro, and in particular when $R_4$ is bromo, the molecule gains affinity for the 5-HT$_7$ receptor subtype. By virtue of this property, use of the compound named ST 1938 is indicated for the treatment of depression, migraine and hypertension, in particular, to facilitate and improve learning processes of the individuals, and to counteract the desynchronisation of human biological rhythms which bring about mental fatigue, depression and sleep disorders.

Inhibition of binding to 5-HT$_6$ receptors was determined according to a published method (Monsma, F. J. et al., *Molecular Pharm.,*1993, 43:320–327). The binding assay has been performed employing rat 5-HT$_6$ stably transfected to HEK293 (human embrionic kidney cells) with [$^3$H]-LSD (lysergic acid diethylamide) as radioligand. Previously, each compound was dissolved in DMSO to prepare 10 mM stock solution, and then dissolved in H$_2$O to a final concentration of 0.1 mM. After serial dilutions, eight different concentrations (from 10 μM to 0.001 nM) in duplicate were employed to obtain a competition curve by which to evaluate binding affinity for 5-HT$_6$ receptor of each test compound. Experimental conditions provided for: 2 nM [$^3$H]-LSD, 100 μM serotonin creatinine sulfate to define non-specific binding and 60 minutes, at 37° C., for incubation of each sample. Following incubation, the membranes were rapidly filtered under vacuum through glass fiber filters (GF/B, Packard). Bound radioactivity was measured with a scintillation counter (Topcount, Packard) using a liquid scintillation cocktail (Microscint 0, Packard). The IC$_{50}$ of each compound were determined by non-linear regression analysis of the com-petition curves using Hill equation curve fitting. Then, these values were employed to calculate inhibition constant (Ki) values by which each test compound affinity for 5-HT$_6$ receptor was expressed. The Ki value was defined by the Cheng Prusoff equation: Ki=IC$_{50}$/1+([L]/Kd) in which IC$_{50}$ value is that concentration (nM) of test compounds by which 50% of specific radioligand is displaced from receptor, [L] is the concentration of the specific radioligand in assay and the Kd is the affinity of radioligand for the receptor.

Displacement experiments were carried out in order to determine the affinity of the substance to the 5-HT$_7$ receptor, according to published method (Shen, Y. et al. (1993) *Journal Biological Chemistry* 268: 18220–18204). For the performance of the test, human 5-HT$_7$ receptor stably transfected to CHO cells (human ovarian cells) were employed and [$^3$H]-LSD (4 nM) as radioligand. Further experimental conditions provided for 10 μM serotonin as non-specific ligand and 120' at 22° C. for incubation of each sample. The respective test compounds were investigated at 8 different concentrations (from $10^{-5}$ M to $10^{-12}$ M) in duplicate, to obtain full competition curve. Each compound was previously dissolved in DMSO to obtain a $10^{-3}$ M stock solution, and then dissolved in H$_2$O to final concentration of $10^{-5}$ M. The binding reaction of each test compound was interrupted by a rapid filtration under vacuum through glass fiber filters (GF/B, Packard). The filters were then washed several times with an ice-cold buffer. Bound radioactivity was measured with a scintillation counter (Topcount, Packard) using a liquid scintillation cocktail (Microscint 0, Packard). As described above, IC$_{50}$ values were determined by non-linear regression analysis of each competition curve and Ki values were calculated from the Chen Prusoff equation (Ki=IC$_{50}$/(1+L/Kd).

In table 1, 5-HT$_6$ and 5-HT$_7$ binding affinity values of each test compound are reported.

TABLE 1

Affinity for 5-HT$_6$ e 5-HT$_7$

| Compounds | 5-HT$_6$ | | 5-HT$_7$ | |
| --- | --- | --- | --- | --- |
| | IC$_{50}$ (nM) | Ki (nM) | IC$_{50}$ (nM) | Ki (nM) |
| ST 1936 | 62 | 31 | 527 | 168 |
| ST 1938 | 62 | 32 | 158 | 47 |
| ST 2253 | 52 | 26 | >1000 nM | >1000 nM |
| Serotonin | 171 | 87 | 0.64 | 0.19 |

ST 1936, ST 1938, ST 2253 display high affinity for rat recombinant 5-HT$_6$ receptor. In addition, their binding affinity is also greater than that observed for Serotonin.

Among these compounds, the one named ST 1938 also displays highest affinity for human recombinant 5-HT$_7$ receptor, whereas ST 1936 and ST 2253 show respectively moderate and negligible affinity.

Selected compounds were examined to determine their specificity of binding to 5-HT$_6$ receptor. Previously, binding affinity for other serotonin sites was evaluated.

In table 2, the affinity values (Ki, nM) of selected compounds to several serotonin subtypes are represented.

TABLE 2

Affinity (Ki, nM)

| | ST 1936 | ST 1938 | ST 2253 | Reference | Compounds |
| --- | --- | --- | --- | --- | --- |
| 5-HT$_6$ | 31 | 32 | 26 | serotonin | 171 |
| 5-HT$_7$ | 168 | 47 | >1 μM | serotonin | 0, 19 |
| 5-HT$_{1a}$ | >1 μM | 947 | 1 μM | 8-OH-DPAT | 3 |
| 5-HT$_{1b}$ | >1 μM | >1 μM | >1 μM | serotonin | 15, 4 |
| 5-HT$_{1d}$ | >1 μM | >1 μM | >1 μM | serotonin | 1, 41 |
| 5-HT$_{2a}$ | >1 μM | >1 μM | >1 μM | Ketanserin | 0, 93 |
| 5-HT$_{2b}$ | >1 μM | 154 | 84 | serotonin | 16 |
| 5-HT$_{2c}$ | >1 μM | >1 μM | >1 μM | mesulergine | 0, 56 |
| 5-HT$_3$ | >1 μM | >1 μM | >1 μM | MDL72222 | 10, 3 |
| 5-HT$_4$ | >1 μM | >1 μM | >1 μM | serotonin | 57, 5 |
| 5-HT$_{5a}$ | >1 μM | >1 μM | >1 μM | serotonin | 156 |
| 5-HT transporter | >1 μM | >1 μM | >1 μM | zimelidine | 9, 28 |

It is shown that the compounds ST 1936 and ST 2253 are able to bind, selectively, 5-HT$_6$ receptors. Furthermore, 5-HT$_6$ receptor binding specificity of ST 1936 and ST 2253 was examined after evaluating binding affinity to some receptors related to other neurotransmitters.

ST 1936 and ST 2253 were examined at 23 sites. At most of these receptors the selected compounds displayed negligible affinity. In particular, affinity values of ST 1936 and ST 2253 appeared similar or greater than 1000 nM for the following receptors: alpha$_{1a}$ and beta$_1$ adrenergic; D$_1$, D$_2$, D$_3$, D$_{4,4}$, D$_5$ dopaminergic; NMDA, muscarinic (non-selective); N neuronal (α-BGTX-sens.), N neuronal (α-BGTX-ins.) nicotinic, H$_1$ histaminergic, opiate (non-selective), V$_{1a}$, V$_{1b}$, V$_2$ of vasopressin, ML$_1$ and ML$_2$ of melatonin, NA transporter, DA transporter. Further the compounds displayed moderate affinity for alpha$_{1b}$ adrenergic receptor 53 nM and 69 nM respectively for ST 1936 and ST 2253. However, interaction capability for alpha$_{1b}$ receptors of selected compounds were about 2 fold and 3 fold lower than that was evaluated for 5-HT$_6$ receptor. Whole data demonstrate that the compounds ST 1936 and ST 2253 have a selective affinity for 5-$HT_6$ receptor.

Relatively to selected compound named ST 1938 which appeared with mixed activity for 5-$HT_6$ and 5-$HT_7$ serotonin receptors, it displayed negligible affinity (Ki>1000 nM) for these sites: $H_1$; NMDA; PCP; muscarinic receptors; nicotinic receptors, opiate; vasopressin $V_1$ and $V_2$; $D_1$, $D_2$, $D_3$, $D_{4,4}$ $D_5$; DA transporter, NA transporter.

A further object of the present invention relates to pharmaceutical compositions comprising, as active ingredient, at least one Formula (I) com-pound, singularly or in association with one or more other Formula (I) compounds, or said Formula (1) compound/s in association with other active ingredients used in the treatments of the pathologies described herein, for example other products with activities for the 5-$HT_6$ and/or 5-$HT_7$ serotoninergic receptors, either as separate dosages or in forms adapted for combined therapy. The active ingredient according to the present invention will be mixed with the appropriate vehicles and/or excipients commonly used in pharmaceutical techniques, as for example, these described in *Remington's Pharmaceutical Sciences Handbook*, latest edition. The compositions according to the present invention will contain a therapeutically effective amount of the active ingredient. The dosage will be determined by those skilled in the art, for example the clinic or the doctor according to the type of pathology being treated and the conditions of the patients, or in accordance with the administration of other active ingredients.

Examples of pharmaceutical compositions are those which allow oral, parenteral, intravenous, intramuscular, subcutaneous, transdermal administration.

Pharmaceutical compositions suited to this purpose are pills, rigid or soft capsules, powders, solutions, suspensions, syrups, solid forms for extemporary liquid composition. Compositions for parenteral administration are, for example, all the injectable forms, whether intramuscular, intravenous, subcutaneous, in the form of solutions, suspensions and emulsions. Liposomal formulations are also mentioned. Controlled release forms of the active ingredient are also included, both for oral administration, such as these coated with the appropriate coating materials, microencapsulated powders, cyclodextrin complexes, and depot forms such as for subcutaneous use or for use as implants.

The invention claimed is:

1. A method of selectively interacting with the 5-$HT_6$ and/or 5-$HT_7$ serotonin receptors comprising administering to a subject in need thereof an effective amount of a compound of Formula (I)

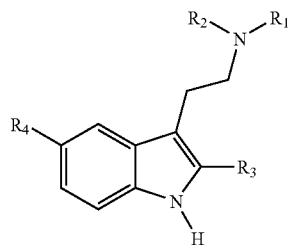

wherein:
$R_1$ and $R_2$, the same or different, are H or $C_1$–$C_6$ linear or branched alkyl;
$R_3$=$C_1$–$C_6$ linear or branched alkyl;
$R_4$=halogen; and of the pharmaceutically acceptable salts thereof.

2. The method according to claim 1, wherein said selective interaction treats nervous system pathologies associated with serotonin level deficit, systemic pathologies involving the cardiovascular system, and systemic pathologies involving the gastrointestinal tract.

3. The method, according to claim 2, wherein hypertension is treated.

4. The method according to claim 2, wherein irritable bowel disease is treated.

5. The method according to claim 1, wherein the method treats migraine, depression, hypertension, psychosis and symptoms arising from the desynchronisation and/or loss of circadian rhythms.

6. The method according to claim 1, wherein ligands of the 5-$HT_6$ serotoninergic receptor and are used in the treatment of depression, mood disorders, psychosis, schizophrenia, motor disorders, cognitive disorders, Parkinson's disease, Alzheimer's disease, or Huntington's disease.

7. The method according to claim 1, wherein in the compound of Formula (I) $R_1$ is the same as to $R_2$.

8. The according to claim 1, wherein in the compound of Formula (I), $R_3$ is methyl and $R_4$ is bromo or chloro.

9. The method according to claim 1, wherein in the compound of Formula (I) $R_4$ is bromo.

10. The method according to claim 9, wherein the compound is 5-bromo-2-methyl-N,N-dimethyltryptamine.

11. The method according to claim 1, wherein the compound $R_4$ is chloro.

12. The method according to claim 11, wherein the Formula (I) compound is 5-chloro-2-methyl-N,N-dimethyltryptamine or 5-chloro-2-ethyl-N,N-dimethyltryptamine.

13. The method according to claim 9, wherein the compounds are ligands of the 5-$HT_7$ serotoninergic receptor.

14. The method according to claim 11, wherein the compounds are ligands of the 5-$HT_6$ serotoninergic receptor.

15. The method according to claim 13 wherein the method treats depression, migraine, hypertension, assists or improves the individual learning processes or counteracts the desynchronisation of human biological rhythms giving rise to mental fatigue, depression and sleep disorders.

16. The method according to claim 14 wherein the method treats depression, mood disorders, psychosis, schizophrenia, motor disorders, cognitive disorders, Parkinson's disease, Alzheimer's disease, or Huntington's disease.

17. A compound of the formula

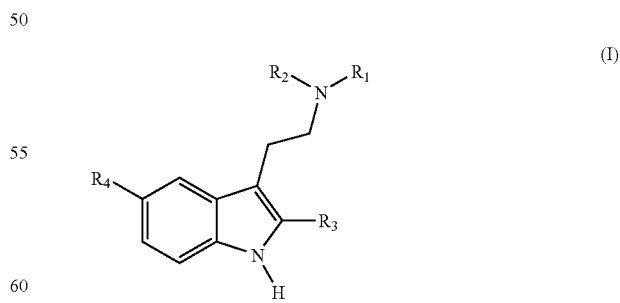

wherein:
$R_1$ and $R_2$, the same or different, are H or $C_1$–$C_6$ alkyl;
$R_3$=$C_1$–$C_6$ alkyl;
$R_4$=halogen, or a pharmaceutically acceptable salt thereof, with the proviso that when $R_4$ is fluoro, chloro or bromo, R$_3$ is methyl, R$_1$ and R$_2$, either the same or different, are not H or methyl.

18. A process for the preparation of the compounds according to claim 17, according to the following scheme:

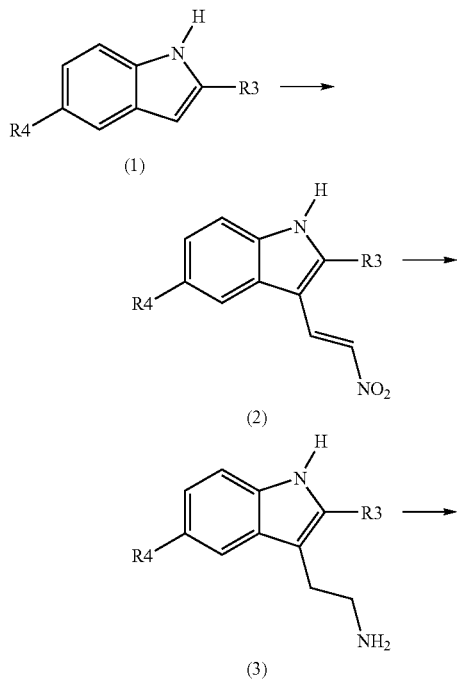

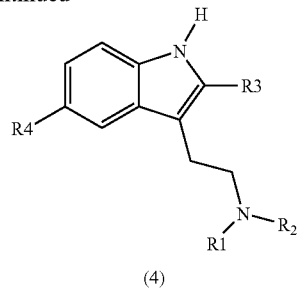

said process comprsing:
  a) reacting 5-halo-2-alkyl-indole (1) with 1-dimethylamino-2-nitroethylene in trifluoroacetic acid to give compound (2):
  b) subjecting compound (2) to reduction of the ethyl double bond adjacent to the nitro group, to give the corresponding saturated derivative (3); and
  c) carrying out functionalisation of the primary amino group in compound (3) with the groups given in the definitions for R$_1$ and R$_3$.

19. A pharmaceutical compositions comprising at least one compound of claim 17 as the active ingredient, admixed with a pharmaceutically acceptable vehicles and/or excipient.

* * * * *